United States Patent [19]
Bergersen

[11] Patent Number: 5,203,695
[45] Date of Patent: Apr. 20, 1993

[54] ORTHODONTIC DEVICE FOR EXPANSION OF ARCHES WITH IMBEDDED WIRE

[76] Inventor: Earl O. Bergersen, 950 Green Bay Rd., Winnetka, Ill. 60093

[21] Appl. No.: 811,575

[22] Filed: Dec. 20, 1991

[51] Int. Cl.⁵ .................................................. A61C 3/00
[52] U.S. Cl. ............................................ 433/6; 433/24; 128/861
[58] Field of Search ................... 433/6, 24; 128/861

[56] References Cited

U.S. PATENT DOCUMENTS

| | | | |
|---|---|---|---|
| 2,678,043 | 5/1954 | Stark | 128/681 |
| 3,478,742 | 11/1969 | Bohlmann | 128/861 X |
| 3,848,335 | 11/1974 | Bergersen | 32/14 |
| 3,898,736 | 8/1975 | Bergersen | 32/14 B |
| 3,939,598 | 2/1976 | Bergersen | 32/14 B |
| 3,950,851 | 8/1976 | Bergersen | 32/14 B |
| 3,967,379 | 7/1976 | Bergersen | 32/14 B |
| 4,055,895 | 11/1977 | Huge | 433/6 |
| 4,073,061 | 2/1978 | Bergersen | 32/14 B |
| 4,337,036 | 6/1982 | Hoffman | 433/6 X |
| 4,433,956 | 2/1984 | Witzig | 433/7 |
| 4,793,803 | 12/1988 | Martz | 433/6 |
| 5,037,295 | 8/1991 | Bergersen | 433/6 |

*Primary Examiner*—Gene Mancene
*Assistant Examiner*—Nicholas D. Lucchesi
*Attorney, Agent, or Firm*—Hill, Steadman & Simpson

[57] ABSTRACT

A tooth positioner which is formed out of molded plastic to conform about arches defined by upper and lower rows of teeth, the positioner being generally U-shaped in plan and H-shaped in cross-section, the positioner having troughs sized and shaped to conform to the arches, the troughs being defined by lingual and labial-buccal flanges joined together by an isthmus including a wire embedded in the lingual flange to alter the shape of at least one of the arches.

15 Claims, 1 Drawing Sheet

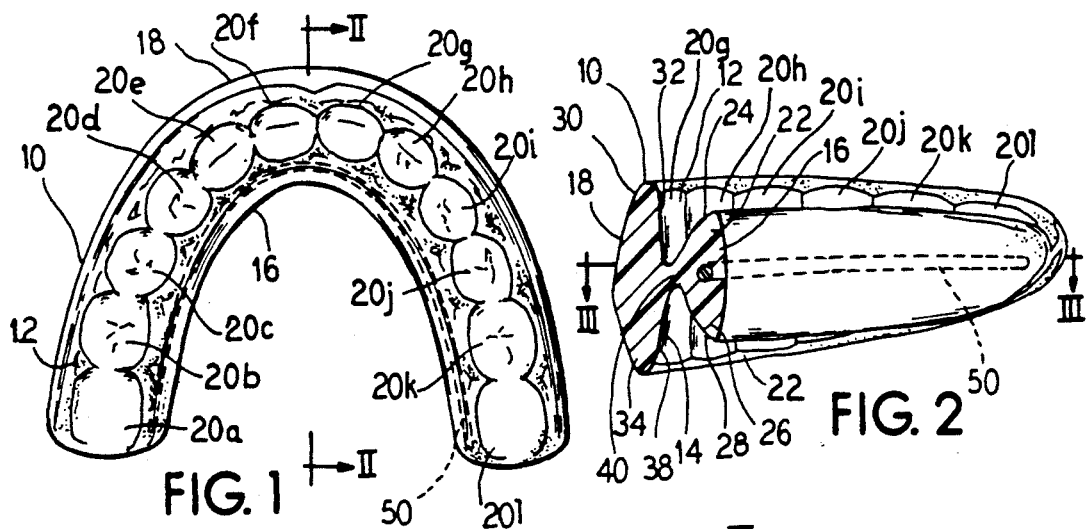
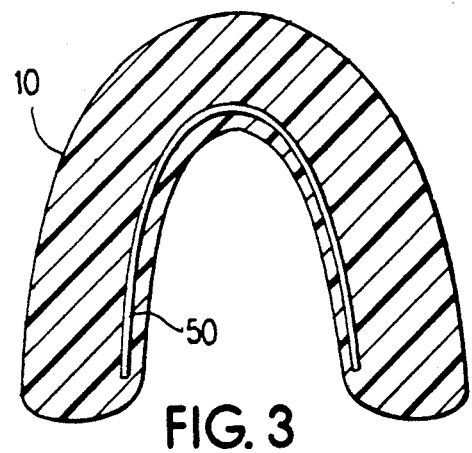
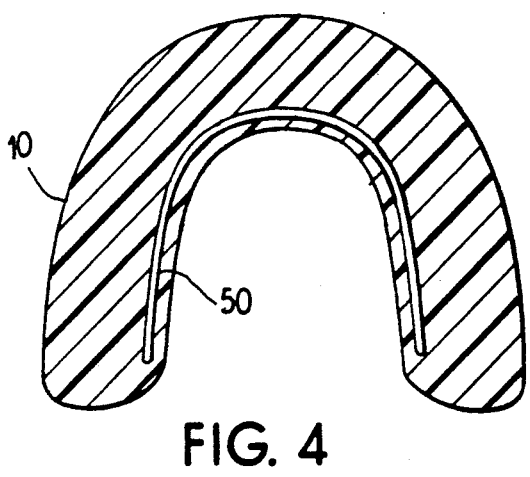
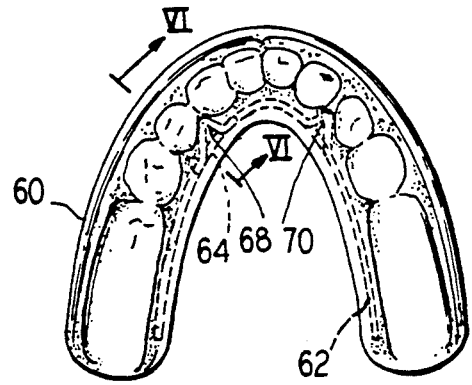
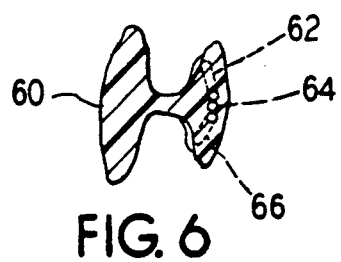

ORTHODONTIC DEVICE FOR EXPANSION OF ARCHES WITH IMBEDDED WIRE

BACKGROUND OF THE INVENTION

The present invention generally relates to devices for positioning teeth. More specifically, the invention relates to molded retainers for positioning or repositioning teeth.

The relevant technology is generally represented by my prior U.S. Pat. Nos. 3,848,335; 3,898,736; 3,939,598; 3,950,851; 3,967,379; 4,073,061; and 4,139,994. These patents generally disclose orthodontic appliances for positioning or repositioning teeth. The appliances comprise molded plastic members that are inserted into the mouth of a wearer. The molded plastic member includes a plurality of sockets arranged in arcuate channels that conform about the teeth of the wearer. The disclosures of these patents are fully incorporated herein by reference.

In the field of orthodontics, conventional orthodontic devices such as bands or the like are often used for straightening teeth to bring them to a predetermined position of proper or close to proper occlusion. To bring teeth into a final position of desired orientation of the mouth, orthodontists will also often use a tooth positioner such as those disclosed and discussed in my prior patents.

SUMMARY OF THE INVENTION

The present invention provides an improved orthodontic appliance. More specifically, the present invention provides an orthodontic appliance for expanding the arches of the teeth of a patient.

To these ends, in an embodiment, the invention provides an orthodontic device comprising a molded plastic member having lingual and labial-buccal flanges, and a wire imbedded in the lingual flange to force expansion or constriction of the arches.

In a preferred embodiment, the wire can be bent to widen or narrow the plastic or rubber device into which it is imbedded. The wire is molded into the material of the device and can be manipulated by hand to alter the shape of the device. However, the wire is sufficiently rigid to exert expansion and constriction forces on the arches of the teeth.

In yet another embodiment, the wire can be imbedded into the material between the arches of the lingual area and can be manipulated so as to alter the anterior arch form, the bi-canine, bicuspid, or molar arch widths, as well as to increase or reverse the curve of Spee in the opposite plane.

In yet another embodiment, additional wires are added to place pressure on individual teeth such as the mesial of the canine to move it distally as expansion occurs, or to engage anterior teeth to provide additional force for rotations such as on the distal-lingual surface of maxillary laterals to make sure they properly rotate.

Accordingly, an advantage of the present invention is the provision of a teeth positioning device for expanding or constricting arches.

Another advantage is a teeth positioning device that can be deformed by hand yet which is sufficiently rigid to exert deformation forces on the arches of teeth.

These and other advantages will become more apparent with reference to the following detailed description and accompanying drawings.

BRIEF DESCRIPTION OF THE DRAWINGS

FIG. 1 is a plan view of a tooth positioner embodying principles of the present invention;

FIG. 2 is a sectional view of the tooth positioner of FIG. 1 taken generally along the line II—II;

FIG. 3 is a sectional view of the tooth positioner of FIG. 2 in an arch constricting formation taken generally along the line III—III;

FIG. 4 is another sectional view of the tooth positioner of FIG. 2 in an arch widening formation taken generally along the line III—III;

FIG. 5 is a plan view of another tooth positioner embodying principles of the invention; and FIG. 6 is a sectional view of the tooth positioner of FIG. 5 taken generally along the line VI—VI.

DETAILED DESCRIPTION OF THE PRESENTLY PREFERRED EMBODIMENTS

In FIG. 1 there is illustrated a retainer or tooth positioner 10 embodying principles of the invention. As illustrated, the retainer 10 is adapted to be inserted into the mouth of the wearer and to conform about the shape of the rows of teeth of the wearer.

The retainer 10, as illustrated in FIGS. 1 and 2, is generally U-shaped in plan so as to conform to typical human mouth configuration and is generally H-shaped in cross-section providing an upper or superior tooth receiving trough 12 and a lower or inferior tooth receiving trough 14. These sides of the troughs 12 and 14 are bounded by a lingual flange 16 which covers the rear of the teeth of the upper and lower arch and a labial and buccal flange 18 which covers the front of the teeth of both arches.

Both the superior and inferior tooth receiving troughs 12 and 14 are provided with a plurality of tooth receiving depressions or sockets, such as sockets 20a through 20l, of different configurations for receiving the teeth of the mouth (upper and lower) from the central incisors through the cuspids and bicuspids, into the first molars and half of the second molar area.

As best illustrated in FIGS. 1 and 2, the lingual flange 16 includes an upper lingual flange 22 which secures the lingual cingulum areas of the upper anterior teeth and lingual surfaces of the lingual cusps of the upper posterior teeth, and includes an inwardly directed rib 24 and covers a portion of the upper lingual gingable area. The flange 16 further includes a lower lingual flange 26 that generally embraces the cingulum area of the lower anterior teeth and the lingual surface of the lingual cusps of the lower posterior teeth and includes an inwardly directed rib 28. The lower lingual flange 26 also extends over a portion of the lower lingual gingable tissue.

As also illustrated in FIGS. 1 and 2, the labial and buccal flange 18 includes a lower labial and buccal flange 30 which covers the labial and buccal surfaces of the lower anterior and posterior teeth. The lower labial and buccal flange 30 includes an inwardly directed rib 32 that extends over a portion of the lower labial and buccal gingival tissue. The flange 18 further includes an upper labial and buccal flange 34 with an inwardly directed rib 36 and covers the entire labial and buccal surfaces of the upper anterior and posterior teeth and also embraces a small portion of the upper gingival tissue.

The several ribs 24, 28, 32, and 36 generally follow the outline of the juncture of the teeth and the gingival tissue.

A retainer such as a retainer 10 can be custom-formed by being molded about a model set of teeth wherein notches are cut closely adjacent the juncture of the teeth and the gingival tissue so that when the retainer is formed by molding same about the teeth of the mold, the ribs would be so formed. However, it is not intended that notches would be formed in the teeth of a patient but rather these ribs would generally fit into the reduced area of the teeth adjacent the juncture of the teeth and the tissue. These ribs provide a means for holding the retainer in place of a patient's mouth without the need for auxiliary fastening devices or the like. These ribs also aid in the retention of torque of the anterior teeth by placing pressure apically in the gingaval third of the labial surface while maintaining incisal edge in a stable position as the fulcrum.

Alternatively, tooth positioners such as the tooth positioner 10 can be mass produced in a mold by means of an appropriate machine. These tooth positioners would necessarily be of a general configuration so as to fit the teeth of a wide cross-section of persons. However, the general appearances would be similar to that of the tooth positioner 10.

The various sockets, such as the sockets 20a to 20l, in the retainer 10 for the upper and lower teeth, are made so that the teeth are snugly embraced by the retainer 10. An isthmus 40 which joins the lingual/buccal or labial halves of the retainer 10 is generally thin, though it differs in dimension between the posterior region and the anterior region so as to resemble the normal relaxed clearance between the teeth, with the exception that the isthmus 40 is slightly thinner in the posterior region. This enables all of the occlusal and incisal surfaces of the teeth to be in contact with the positioner at the same time when occlusal pressure is applied. Any change which might be made would be to increase the thickness of the isthmus 40 in the anterior region to enable a corrected anterior vertical overbite to be effectively retained or to effect such correction.

The retainer 10 is preferably made out of a semiresilient plastic material, preferably a transparent material. The transparency enables a dental practitioner to actually see where the tooth movement will take place by observing blanching tissue around the teeth and also enables the dental practitioner to detect a potential soft tissue or some sore spots due to abnormal impingement of the flanges of the retainer 10.

The retainer 10 illustrated in FIGS. 1 through 4 further includes a wire 50 imbedded in the lingual flange 16. This wire provides for constriction or expansion of the arches of the teeth. As illustrated most clearly in FIG. 3, the wire can be bent to constrict the shape of the arches. In FIG. 4, it is illustrated that the wire can be bent more widely by manual force so as to expand the arches.

The wire 40 can be molded into a preformed retainer 10 or into a custom-made retainer 10.

It can be appreciated that although the wire 40, and accordingly the retainer 10, can be deformed by hand, the wire 40 is sufficiently rigid to exert the appropriate constriction or expansion forces necessary to deform an arch of teeth. Thus, as an arch of teeth is deformed, i.e., caused to expand, contract, to change its curve of Spee, etc., the retainer 10 can be reshaped by an orthodontist so as to continue the deformation by providing appropriate forces. For example, the orthodontist can periodically widen the retainer 10 as an arch of teeth widens.

In FIGS. 5 and 6, there is illustrated a retainer 60 embodying further principles of the invention. The retainer 60 generally is constricted in manner similar to that of the retainer 10. However, the retainer 60 includes several wires in place of the wire 40.

As illustrated, three wires 62, 64, and 66 are imbedded within the lingual flange 68 of the retainer 60. The wire 64 is similar in position and shape to the wire 40, described above. The wires 62 and 66 are added to place pressure in individual teeth such as the mesial of the canine to move it distally as expansion occurs or to engage anterior teeth to provide additional force for rotation such as on the distal-lingual surface of maxillary laterals to make sure they properly rotate.

To this end, the wire 62 includes sharp and jutting bends 68 and 74. These bends 68 and 74 engage between the ends of preselected teeth to place the individualized pressure. The wire 66 can also include such bends.

While a preferred embodiment has been shown, modifications and changes may become apparent to those skilled in the art which shall fall within the spirit and scope of the invention. It is intended that such modifications and changes be covered by the attached claims.

I claim as my invention:

1. An orthodontic appliance, comprising:
   (a) a tooth positioner, the tooth positioner being generally U-shaped in plan, the tooth positioner having a trough sized and shaped to receive a row of teeth arranged in an arch, the trough being defined by lingual and labial-buccal flanges joined together by an isthmus, the tooth positioner being made of molded plastic; and
   (b) deformable means embedded in the positioner for deforming the arch defined by the row of teeth, the deformable means providing forces for one of constriction and expansion of the arch, the deformable means also comprising means for pressuring an individual tooth to move distally as the arch is deformed, the deformable means comprising at least one wire, said at least one wire being bendable after the appliance is made to provide additional force beyond that which originally is available and which has been made for a given arch width, said at least one wire being positioned in the lingual flange, the positioner including a plurality of ribs that generally follow the outline of the junctures of the teeth and gingival tissue to provide means for holding the positioner in place in a patient's mouth without the need for auxiliary fastening devices, the positioner including a plurality of sockets in which the teeth are snugly embraced, said at least one wire including at least one sharp and jutting bend which engages between ends of preselected teeth to place pressure on the individual tooth which is to move distally as the arch is deformed.

2. The appliance of claim 1, wherein the positioner is H-shaped in cross-section and includes two troughs for receiving teeth, one trough for an upper row of teeth, the other trough for a bottom row of teeth.

3. The appliance of claim 1, said at least one wire comprises a metal wire.

4. The appliance of claim 1, wherein the deformation of the arch comprises alteration of at least one of: an anterior arch form; bi-canine width; bicuspid width; and molar arch width.

5. The appliance of claim 1, wherein the deformation includes increasing or reversal of the curve of Spee of the arch.

6. The appliance of claim 1, wherein the plastic is transparent.

7. The appliance of claim 1, wherein said at least one wire comprises a plurality of wires.

8. An orthodontic appliance, comprising:
(a) a tooth positioner, the tooth positioner being generally U-shaped in plan and H-shaped in cross-section, the tooth positioner having upper and lower troughs sized and shaped to receive upper and lower rows of teeth arranged in arches, the troughs being defined by lingual and labial-buccal flanges joined together by an isthmus, the positioner including a plurality of ribs that generally follow the outline of the junctures of the teeth and gingival tissue to provide means for holding the positioner in place in a patient's mouth without the need for auxiliary fastening devices, the positioner including a plurality of sockets in which the teeth are snugly embraced; and at least one wire embedded in the lingual flange, said at least one wire operatively serving to deform at least one of the arches defined by the rows of teeth, said at least one wire also including means for pressuring an individual tooth to move distally as the arch is deformed said at least one wire being made of metal, the wire being bendable after the appliance is made to provide additional force beyond that which originally is available and which has been made for a given arch width, said at least one wire including at least one sharp and jutting bend which engages between ends of preselected teeth to place the pressure on the individual tooth which is to move distally as the arch is deformed.

9. The appliance of claim 8, wherein the deformation includes alteration of at least one of: a width between bi-canine teeth, bicuspid teeth, and molars; an anterior arch form; and the curve of Spee.

10. The appliance of claim 8, wherein the tooth positioner is made of molded plastic.

11. The appliance of claim 10, wherein the plastic is transparent.

12. The appliance of claim 8, comprising a plurality of wires embedded in the lingual flange, at least one wire operatively serving to deform at least one of the arches defined by one of the rows of teeth, another wire operatively serving to rotate individual teeth as the arch is deformed.

13. An orthodontic appliance comprising:
(a) a molded plastic tooth positioner being generally U-shaped in plan and H-shaped in cross-section, the tooth positioner having upper and lower troughs sized and shaped to receive upper and lower rows of teeth arranged in arches, the troughs being defined by lingual and labial-buccal flanges joined together by an isthmus, the positioner including a plurality of ribs that generally follow the outline of the junctures of the teeth and gingival tissue to provide means for holding the positioner in place in a patient's mouth without the need for auxiliary fastening devices, the positioner including a plurality of sockets in which the teeth are snugly embraced; and at least one metal wire embedded in the lingual flange, the wire operatively serving to deform at least one of the arches by altering a width of the arch at a preselected position, said at least one wire also including means for pressuring an individual tooth to move distally as the arch is deformed, said at least one wire being bendable after the appliance is made to provide additional force beyond that which originally is available and which has been made for a given arch width, said at least one wire including at least one sharp and jutting bend which engages between ends of preselected teeth to place pressure on the individual tooth which is to move distally as the arch is deformed.

14. The appliance of claim 13, wherein the wire selectively operatively serves to alter at least one of: an anterior arch form; bi-canine teeth width; bicuspid teeth width; and molar teeth width.

15. The appliance of claim 13, wherein a plurality of wires are embedded in the lingual flange.

* * * * *